United States Patent
Choi et al.

(10) Patent No.: US 7,387,027 B2
(45) Date of Patent: Jun. 17, 2008

(54) CHARACTERIZATION OF MATERIALS WITH OPTICALLY SHAPED ACOUSTIC WAVEFORMS

(75) Inventors: Jaime D. Choi, Somerville, MA (US); Benjamin Paxton, Cambridge, MA (US); Thomas Feurer, Bern (CH); Masashi Yamaguchi, Green Island, NY (US); Keith A. Nelson, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 463 days.

(21) Appl. No.: 11/186,401

(22) Filed: Jul. 21, 2005

(65) Prior Publication Data

US 2006/0027021 A1    Feb. 9, 2006

Related U.S. Application Data

(60) Provisional application No. 60/590,684, filed on Jul. 23, 2004.

(51) Int. Cl.
  *G01N 29/00* (2006.01)
  *G01F 2/02* (2006.01)
  *G01B 11/02* (2006.01)
(52) U.S. Cl. ............... 73/668; 73/649; 73/655; 356/502; 356/503; 359/331
(58) Field of Classification Search ........... 73/649, 73/64.43, 655, 801; 356/502, 503; 359/331
  See application file for complete search history.

(56) References Cited

U.S. PATENT DOCUMENTS

| | | | |
|---|---|---|---|
| 5,148,318 A * | 9/1992 | Okamoto et al. ........... 359/629 |
| 5,239,548 A * | 8/1993 | Babbitt et al. ............ 372/26 |
| 5,541,947 A | 7/1996 | Mourou et al. |
| 5,589,936 A | 12/1996 | Uchikawa et al. |
| 5,682,262 A | 10/1997 | Wefers et al. ............ 359/305 |
| 5,719,650 A | 2/1998 | Wefers et al. ............ 349/74 |
| 6,201,916 B1 | 3/2001 | Eggleton et al. |
| 6,219,142 B1 | 4/2001 | Kane |
| 6,456,380 B1 | 9/2002 | Naganuma |
| 6,552,301 B2 * | 4/2003 | Herman et al. ......... 219/121.71 |
| 6,734,982 B2 * | 5/2004 | Banet et al. ............ 356/630 |
| 6,930,779 B2 | 8/2005 | McGrew |
| 2006/0016790 A1 * | 1/2006 | Yeik ................ 219/121.61 |

(Continued)

OTHER PUBLICATIONS

Beers et al., "Ultrahigh frequency acoustic phonon generation and spectroscopy with Deathstar pulse shaping", *Optical Society of America*, pp. 236-238 (2004).

(Continued)

*Primary Examiner*—Hezron Williams
*Assistant Examiner*—Jacques M. Saint-Surin
(74) *Attorney, Agent, or Firm*—Fish & Richardson P.C.

(57) ABSTRACT

A method for characterizing one or more properties of a sample using acoustic waveforms is disclosed, and comprises directing a sequence of at least three optical pulses to the sample to generate an acoustic response in the sample at a frequency corresponding to the pulse sequence, varying the timing of one or more of the pulses in the sequence to vary the frequency of the acoustic response in the sample, and measuring the strength of the acoustic response as a function of the varied frequency to determine information about the sample.

28 Claims, 6 Drawing Sheets

U.S. PATENT DOCUMENTS

2006/0293595 A1* 12/2006 Clark et al. ............ 600/437

OTHER PUBLICATIONS

Jaime Dawn Choi, "Generation of Ultrahigh Frequency Acoustic Waves for the Characterization of Complex Materials", *MIT Ph.D. Thesis*, (Jan. 2005).

Kawashima, et al., "Femtosecond Pulse Shaping, Multiple-Pulse Spectroscopy, and Optical Control", *Annu. Rev. Phys. Chem*, vol. 46, pp. 627-656 (1995).

Leaird et al., "Femtosecond Direct Space-to-Time Pulse Shaping", *IEEE Journal of Quantum Electronics*, vol. 37, No. 4, pp. 494-504 (Apr. 2001).

Matsuda et al., "Narrowband Generation of Ultrafast Acoustic and Thermal Transients in Thin Films for Enhanced Detectability", *IEEE Transactions on Ultrasonics, Ferroelectrics, and Frequency Control*, vol. 49, No. 7, pp. 915-921 (Jul. 2002).

Maznev et al., "Optical heterodyne detection of laser-induced gratings", *Optics Letters*, vol. 23, No. 16, pp. 1319-1321 (Aug. 15, 1998).

Morath, et al., "Phonon attenuation in amorphous solids studied by picosecond ultrasonics", *Physical Review B*, vol. 54, No. 1, pp. 203-213 (Jul. 1, 1996).

Nelson et al., "Laser-induced phonon spectroscopy. Optical generation of ultrasonic waves and investigation of electronic excited-state interactions in solids", *Physical Review B*, vol. 24, No. 6, pp. 3261-3275 (Sep. 15, 1981).

Özgür et al., "Control Coherent Acoustic Phonons in Semiconductor Quantum Wells", *Physical Review Letters*, vol. 86, No. 24, pp. 5604-5607 (Jun. 11, 2001).

Saito et al., "Picosecond acoustic phonon pulse generation in nickel and chromium", *Physical Review B*, vol. 67 (2003).

Siders et al., "Efficient high-energy pulse-train generation using a 2"-pulse Michelson interferometer", *Applied Optics*, vol. 37, No. 22, pp. 5302-5305 (Aug. 1, 1998).

Slayton et al., "Picosecond acoustic transmission measurements. I. Transient grating generation and detection of acoustic responses in thin metal films", *Journal of Chemical Physics*, vol. 120, No. 8, pp. 3908-3918 (Feb. 22, 2004).

Slayton et al., "Transient grating measurement of film thickness in multilayer metal films", *Journal of Applied Physics*, vol. 90, No. 9, pp. 4392-4402 (Nov. 1, 2001).

Zhu et al., "Attenuation of longitudinal-acoustic phonons in amorphous $SiO_2$ at frequencies up to 440 GHz", *Physical Review B*, vol. 44, No. 9, pp. 4281-4289 (Sep. 1, 1991).

* cited by examiner

A=Al
B=SiO₂
C=Al

CHARACTERIZATION OF MATERIALS WITH OPTICALLY SHAPED ACOUSTIC WAVEFORMS

CROSS-REFERENCE TO RELATED APPLICATIONS

This application claims priority to U.S. Application Ser. No. 60/590,684 entitled "Characterization of Materials with Optically Shaped Acoustic Waveforms", filed on Jul. 23, 2004, the contents of which are incorporated herein by reference.

STATEMENT AS TO FEDERALLY SPONSORED RESEARCH

This invention was made with Government support under NSF CHE-0212375 and DOE DE-FG02-00ER15087. The Government has certain rights in this invention.

TECHNICAL FIELD

The invention relates to material characterization using acoustic techniques. For example, the invention relates to using pulse shaping methods to produce acoustic waveforms for the characterization of one or more frequency-dependent properties of a sample.

BACKGROUND

Acoustic waves may be used to characterize surface and bulk properties of materials, including film thickness in layered materials, material stiffness (elastic modulus), and sound velocity. Photoacoustic methods have been applied to the characterization of mesoscopic structures (which may have properties that differ from their bulk counterparts) and to the nondestructive, non-contact probing of subsurface structural elements and defects in opaque materials. Applications of photoacoustic spectroscopy are described, for example, in "Picosecond acoustic phonon pulse generation in nickel and chromium," *Physical Review B* 67, 205421 (2003) by T. Saito, O. Matsuda and O. B. Wright, and in "Transient grating measurements of film thickness in multilayer metal films," *Journal of Applied Physics* 90, 4392-4402 (2001) by R. M. Slayton, K. A. Nelson and A. A. Maznev, the contents of both of which are incorporated herein by reference.

Time-resolved sample characterization using acoustic waves is initiated in some cases by first generating an acoustic wave at the surface of a sample through absorption of an incident optical waveform. Absorption may lead to the generation of surface acoustic waves that propagate along the material surface, or in thin layers at or near the surface. Absorption may also lead to the generation of acoustic waves, such as longitudinal waves, that propagate into the bulk of the sample. Acoustic waves may also be introduced into the bulk region of the sample through direct absorption of an incident waveform in the bulk region.

In some cases, in order to generate acoustic waves through absorption at or near a surface, one or more optical pulses are employed. The pulses are short in duration relative to the inverse of the acoustic frequency of interest, and are at a wavelength that is strongly absorbed at the surface of the material through which the acoustic wave propagates. Absorption of a short-duration optical pulse by a sample heats the sample and launches an acoustic pulse, which may be thought of as an acoustic wavepacket. Such a wavepacket may include, for example, from one-half to one complete acoustic cycle. Consequently, the wavepacket may include a broad distribution of acoustic frequency and wavevector components. Broadband acoustic wavepackets with frequency components up to about 500 GHz may be generated, for example, through optical irradiation of a thin aluminum film by a subpicosecond laser pulse.

Broadband acoustic pulses may be used to study the structure of material samples. Partial reflections of a broadband acoustic waveform occur at external and, if present, internal sample interfaces, and are due to the acoustic impedance mismatch of the materials which form the interface. The partial reflections may be detected as "echoes" at a sample external surface. For example, detection of acoustic waveforms reaching the surface of the sample may involve the time-resolved measurement of strain-induced changes in reflectivity of a transducer layer on the surface of the sample. The response of a sample to a broadband acoustic waveform may alternatively be detected by coherent scattering of a measurement pulse, or by interferometry. Transformation of a time-resolved sample measurement signal to the frequency domain may permit the study of one or more frequency-dependent properties of the sample. At very high acoustic frequencies, the sensitivity of broadband acoustic methods may be limited by the signal-to-noise ratio of the measurement data, and by the ease with which unambiguous frequency-dependent sound velocities, damping rates, and other sample parameters may be extracted from the measurement data.

Narrowband acoustic measurements, in contrast to broadband measurements, may be employed to determine the acoustic velocity, damping rate, and/or other properties of a sample at, nominally, one or more specific acoustic measurement frequencies. The signal-to-noise ratio of narrowband measurements may be relatively high, since all of the acoustic energy is concentrated in a narrow frequency band. High acoustic frequencies are of particular interest, since they provide greater resolution in photoacoustic spectroscopy. When the frequency $\omega$ of a narrowband acoustic pulse, propagating at velocity $v_s$ within a sample, is tuned such that the inverse of the frequency corresponds to a characteristic relaxation time $\tau_c$ of the sample ($\tau_c\omega \sim 1$), the acoustic velocity and attenuation rate change in a manner which yields structural and other information about the sample. A similar condition holds if the inverse of the acoustic wavevector $q=\omega/v_s$ approaches the order of a structural element of size d (qd~1). At higher frequencies, faster responses and smaller structural properties of a sample may be measured using narrowband acoustic waveforms.

Generation of tunable, narrowband acoustic pulses through optical means has long been possible at megahertz frequencies by employing techniques such as impulsive stimulated thermal scattering (ISTS). ISTS is described, for example, in "Laser-induced phonon spectroscopy. Optical generation of ultrasonic waves and investigation of electronic excited-state interactions in solids." *Physical Review B* 24, 3261-3275 (1981) by K. A. Nelson, D. R. Lutz, M. D. Fayer and L. Madison, the contents of which are incorporated herein by reference. The ISTS technique generally includes spatially and temporally overlapping two laser pulses inside a sample, where they form an interference pattern with a spatial periodicity that depends on the angle at which they cross and on the optical wavelength of the pulses. Absorption of the pulses heats the sample, and concurrent rapid expansion launches counter-propagating acoustic waves with an acoustic wavelength that nominally matches the period of the laser interference pattern. Tuning of the acoustic wavelength may be achieved by changing the crossing angle of the two pulses. Acoustic waves with frequencies of tens of MHz to a few GHz may be produced in this manner, Measurement of material properties may be accomplished by monitoring the time-dependent refractive index of the sample. For example, refractive index changes may be monitored by measuring the coherent scattering of a third laser pulse.

Higher frequency, narrowband acoustic pulses at GHz frequencies have been generated using multiple quantum well materials with a specified spatial periodicity, and with materials containing metal films with specified thicknesses which utilize multiple internal reflections. For example, femtosecond optical irradiation of multiple quantum well structures is disclosed in "Control of Coherent Acoustic Phonons in Semiconductor Quantum Wells," *Physical Review Letters* 86, 5604-5607 (2001) by Ü. Özgür, C.-W. Lee and H. O. Everitt, the contents of which are incorporated herein by reference. Acoustic waves at frequencies of about 700 GHz have been generated using this method. The spatial periodicity of the quantum wells determines the nominal frequency of the acoustic wave which is generated, and so a specific quantum well structure is employed to produce a particular acoustic frequency.

Thin metal film structures which have been used to generate narrowband acoustic waves at gigahertz frequencies are disclosed, for example, in "Phonon attenuation in amorphous solids studied by picosecond ultrasonics," *Physical Review B* 54, 203-213 (1996) by C. J. Morath and H. J. Maris, the contents of which are incorporated herein by reference. The structures may include a metal transducer layer deposited onto the surface of a sample of interest. Irradiation of the transducer layer generates a propagating acoustic wave therein. Each time the acoustic wave encounters the interface between the transducer layer and the sample, a portion of the acoustic wave intensity is transmitted through the interface and enters the sample. For every round trip the acoustic wave completes inside the transducer layer, partial transmission into the sample yields an additional "cycle" of a narrowband acoustic waveform. Acoustic waves with frequencies greater than 300 GHz may be generated using this method. Since the acoustic frequency depends upon the metal transducer thickness and sound velocity, a different transducer is used to produce each acoustic frequency of interest.

Measurement of at least one of the intensity, phase, temporal location, frequency spectrum and/or spatial position of a measurement beam following interaction with a sample in which an acoustic wave is propagating yields information which may be used to characterize one or more properties of the sample. For example, measurements of the times-of-flight of an acoustic wave and its partial reflections from sample interfaces may be used to determine the thicknesses of one or more layers comprising the sample. Phase shifts of the measured time-dependent surface displacement for two different known sample thicknesses may be determined in order to calculate the sound velocity at a particular frequency in the sample. The time-dependent intensity of the sample response may be used to determine the acoustic damping rate at a particular frequency. Further, all such measurements may be performed in a manner which is nondestructive to the sample and which involves no sample contact.

SUMMARY

We disclose methods and apparatus for characterizing one or more properties of a material using narrowband acoustic waveforms produced by optical pulse shaping techniques. The method may provide enhancements in the signal-to-noise ratio of the measured sample response due to the concentration of all of the acoustic energy in a narrow frequency range, and under conditions where the frequency of the acoustic waveform matches at least one acoustic resonance frequency of the sample.

In general, in one aspect, the invention features a method including: (i) directing a sequence of at least three optical pulses to a sample to generate an acoustic response in the sample at a frequency corresponding to the pulse sequence; (ii) varying the timing of one or more of the pulses in the sequence relative to one or more other pulses in the sequence to vary the frequency of the acoustic response in the sample; (iii) measuring the strength of the acoustic response as a function of the varied frequency to determine information about the sample.

Embodiments of the method may include any of the following features.

The sequence of optical pulses may include more than three optical pulses. For example, the sequence may include four optical pulses, or more than four optical pulses.

The pulses in the sequence may be temporally spaced by any amount, and the temporal spacings may be uniform or non-uniform. The frequency of the acoustic response may correspond to a frequency of the pulse sequence. For example, the pulses in the sequence may be equally spaced in time from one another, and the frequency corresponding to the pulse sequence may be the inverse of the equally spaced timing between the pulses. Alternatively, for example, the pulses in the sequence may not all be equally spaced in time from one another, and the frequency corresponding to the pulse sequence may be a frequency of a peak in a frequency transform of the time-varying intensity of the pulse sequence.

The optical pulses may include electromagnetic radiation in any spectral region. For example, the optical pulses may include radiation in at least one of the ultraviolet, visible, and/or infrared spectral regions.

The frequencies of the acoustic response may be in a range of frequencies which correspond to a range of pulse timings in the optical pulse sequence. For example, the frequencies of the acoustic response may be in the range 2-2000 GHz. Alternatively, for example, the frequencies of the acoustic response may be in the range 5-500 GHz.

The optical pulses comprising the pulse sequence may each have a pulse width less than about 1 picosecond.

Varying the timing of one or more of the pulses in the sequence may include varying the timing between each pair of consecutive pulses in the pulse sequence. For example, the pulses in the pulse sequence define a repetition rate, and varying the timing between each pair of pulses in the pulse sequence may include varying the repetition rate.

The pulse sequence may be generated by directing a beam including at least one optical pulse to make three or more passes to a partially reflective interface configured to transmit a first portion of the pulse and reflect a second portion of the pulse. For example, the partially reflective interface may be part of a recirculating cavity, and varying the timing of one or more of the pulses in the sequence may include moving one or more of the optics in the recirculating cavity relative to one or more other optics in the recirculating cavity.

The optical pulse may make more than three passes to the partially reflective interface. For example, the pulse may make four passes, or more than four passes, to the partially reflective interface.

The pulse sequence may be generated by filtering spatially dispersed spectral components of an input waveform and recombining the filtered spectral components to form an output waveform that includes the pulse sequence.

The pulses in the sequence may contact the sample at different angles.

Measuring the strength of the acoustic response may include directing an optical probe beam to the sample to interact with the acoustic response. For example, a change in a property of the probe beam caused by its interaction with the acoustic response in the sample may be monitored in order to measure the strength of the acoustic response. The change in the property of the probe beam may be monitored interferometrically, for example. The monitored property of the probe beam may be phase, intensity, direction, or spectral content. The optical probe beam may include one or more optical pulses, such as one pulse, or three pulses, or four pulses, or more. Furthermore, for example, in embodiments in which the optical probe beam includes a probe pulse sequence, the frequency of the pulses in the probe pulse sequence can be selected to match that of the excitation pulse sequence.

The information about the sample may include one or more resonance frequencies of the sample. Alternatively, or in addition, the information about the sample may include information about a thickness of a layer in the sample, a sound velocity in the sample, an acoustic impedance mismatch between layers in the sample, and/or delamination of layers in the sample.

The sample may include a film, and the information about the sample may include a film thickness.

In general, in another aspect, the invention features an apparatus that includes: (i) an optical excitation source configured to direct a sequence of at least three optical pulses to a sample to generate an acoustic response in the sample at a frequency corresponding to the pulse sequence, where the optical excitation source is further configured to vary the timing of one or more of the pulses in the sequence, in order to vary the frequency of the acoustic response in the sample; (ii) an optical detection system configured to measure the strength of the acoustic response as a function of the varied frequency; (iii) an electronic processor coupled to the optical detection system and configured to determine information about the sample based on the measured strength of the acoustic response as a function of the varied frequency.

Embodiments of the apparatus may further include features corresponding to any of those described above in connection with the method.

Unless otherwise defined, all technical and scientific terms used herein have the same meaning as commonly understood by one of ordinary skill in the art to which this invention belongs.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Acoustic spectroscopy in the gigahertz regime involves signal-to-noise levels in measured responses of materials which are sufficiently high that they permit reliable spectral decomposition of the time-resolved signals. For this reason, a narrowband approach to acoustic measurements, in which all of the acoustic energy is concentrated within a small range of wavelengths, may prove advantageous. Extension of narrowband acoustic techniques to the high frequency gigahertz regime also includes methods for generating tunable acoustic waves in samples of interest. By measuring one or more material properties at a single acoustic frequency, and then repeating measurements over a broad frequency tuning range, an extensive characterization of a material sample may be possible.

Tunable generation of narrowband, high frequency acoustic waves in a sample may be realized using optical pulse shaping techniques. The method involves producing an acoustic wave by means of a timed sequence of optical pulses which are absorbed by the material. Local heating of the material in the region of the absorption causes the material to expand, launching an acoustic waveform. The pulses in the sequence may be of equal or nearly equal temporal spacing, so that the acoustic waveform which is generated includes only a narrow range of acoustic frequency components, with the distribution of frequencies centered upon a frequency that corresponds to the repetition rate of the optical pulse sequence. The distribution may also contain harmonics of the central acoustic frequency.

Adjustment of the repetition rate of the optical pulse sequence used to generate the acoustic waveform is used to vary the acoustic frequency. In some samples which contain one or more layers, such as a sandwich structure comprising more than one material, the frequency of the acoustic waveform may be adjusted to match at least one resonance frequency of the sample by adjusting the temporal spacing between the optical pulses used to generate the acoustic waveform. Various properties of the layers may be determined in this manner, including layer thicknesses, resonance frequencies, impedance mismatch at interfaces, elastic properties, delamination, and sound velocity. In general, samples may include metals, crystals, amorphous materials, liquids, and other materials, and samples may include simple or complex structures such as one or more layers, domains, defects, and other structural features.

Figure 1:
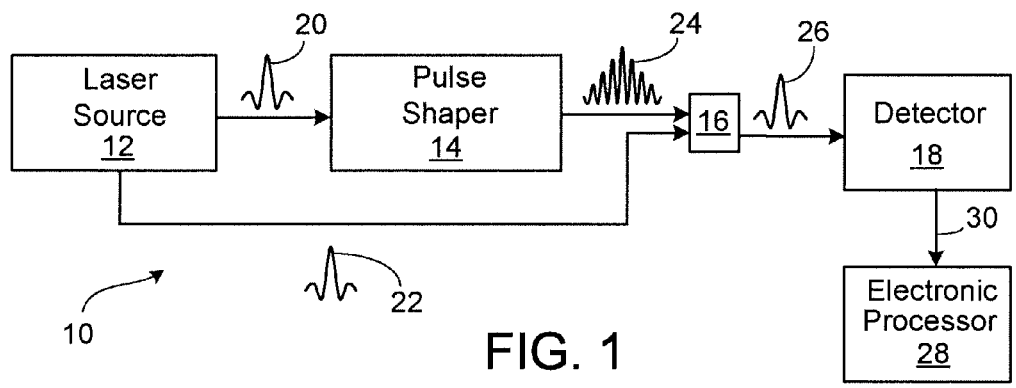
FIG. 1 is a schematic diagram of a system for the characterization of one or more properties of a sample by means of narrowband acoustic waves.

FIG. 1 is a schematic drawing of a system 10 for the characterization of material properties using narrowband acoustic waveforms. The system includes a laser source 12 that provides optical pulses that are used to generate a narrowband acoustic wave in a material, and to measure the material response to the generated acoustic wave. Laser source 12 provides input waveform 20 which enters pulse shaper 14, and is converted by pulse shaper 14 into an excitation waveform 24 which includes a sequence of pulses, where the temporal delay between the individual pulses in excitation waveform 24 may be adjusted.

Excitation waveform 24 is incident upon a sample 16 to be characterized. Absorption by sample 16 of each of the pulses of excitation waveform 24 launches a series of acoustic waves in sample 16 which, cumulatively, comprise a narrowband acoustic waveform at one or more acoustic frequencies. The frequencies contained within the bandwidth of the narrowband acoustic waveform correspond to the inverses of the delay times between the individual pulses in excitation waveform 24, the durations of the individual pulses, and the temporal intensity envelope of excitation waveform 24.

A probe waveform 22 is also provided by laser source 12. Probe waveform 22 may be phase-coherent and may be temporally synchronized and/or delayed with respect to waveform 20 and waveform 24. Probe waveform 22 is employed to monitor the response of sample 16 to the acoustic wave generated by excitation waveform 24, and to measure one or more properties of the sample as a function of acoustic frequency.

Measurement waveform 26 includes a modified form of probe waveform 22, where the modification occurs due to interaction with sample 16, and in response to the generation and propagation of an acoustic wave in sample 16 by excitation waveform 24. The temporal intensity profile and/or phase of measurement waveform 26 may be sensitive to the temporal evolution of one or more properties of sample 16 as a function of acoustic frequency. Measurement waveform 26 is transformed into an electronic signal 30 by detector 18, wherein the electronic signal may be used for further calculation or manipulation. Electronic processor 28, which is electrically connected to detector 18, may include electronic and other hardware components for receiving signal 30, and further hardware and software components for processing signal 30 and determining one or more properties of sample 16 as a function of acoustic frequency, based on the measured acoustic response of the sample extracted from signal 30.

In general, laser source 12 may be any source of optical pulses suitable for generating and an acoustic wave in sample 16 and for measuring one or more properties of sample 16 while the acoustic wave propagates therein. For example, laser source 12 may be a laser oscillator or an amplified laser system.

Input waveform 20 is provided by laser source 12, and may include a single optical pulse, or more than one pulse. Preferably, sample 16 exhibits optical absorption at the central frequency of input waveform 20, and the quantity of absorbed energy is such that an acoustic wave is launched in sample 16, producing a measurable response. The central frequency of input waveform 20 may, in general, be any frequency. For example, the central frequency of input waveform 20 may be in the ultraviolet, visible, or infrared portion of the electromagnetic spectrum. In general, the full-width at half-maximum (FWHM) temporal duration of input waveform 20 is shorter than the peak-to-peak delay times between pulses that comprise excitation waveform 24. The FWHM duration of input waveform 20 may be substantially shorter than the temporal spacing of the pulses in excitation waveform 24. For example, input waveform 20 may be a factor of 2 shorter, or a factor of 10 shorter, or more.

Pulse shaper 14 includes optical elements which convert input waveform 20 into a sequence of pulses which comprise an excitation waveform 24 suitable for generating a narrowband acoustic response in sample 16. For example, pulse shaper 14 may include a recirculating cavity of adjustable length, an output interface such as an output window of spatially varying reflectivity, and a series of output mirrors and focusing optics. Alternatively, for example, pulse shaper 14 may include any other element or combination of elements suitable for producing an output waveform that may be used to generate a narrowband acoustic waveform in sample 16 at a desired acoustic frequency. Pulse shaper 14 may include at least one liquid crystal spatial light modulator (SLM), or a deformable mirror, or a microelectromechanical systems (MEMS) device, and electronic control components, configured to produce an excitation waveform 24 from an input waveform 20. Pulse shaper 14 may additionally include other optical elements such as lenses, polarizers, beamsplitters, and diffractive elements such as diffraction gratings.

In general, pulse shaper 14 generates excitation waveform 24 which includes more than one pulse. For example, excitation waveform 24 may include three pulses, or four pulses, or more. Each pulse may be delayed by the same amount relative to its predecessor, or the delays may vary from one pulse to the next within excitation waveform 24. For example, if the delays between pulses comprising excitation waveform 24 are the same or nearly the same, excitation waveform 24 may produce an acoustic waveform with, nominally, a single frequency component. Alternatively, for example, if the delays between pulses included in excitation waveform 24 vary individually for each of the pulses relative to its predecessor, excitation waveform 24 may produce an acoustic waveform that includes multiple frequency components. The sequence of pulses comprising excitation waveform 24 may be periodic, or may be aperiodic, and may include pulses that have irregular temporal spacings.

If excitation waveform 24 produces in sample 16 an acoustic waveform which includes multiple frequency components, the multiple frequency components may be used to characterize a sample 16 which includes multiple material layers of the same or different thickness, composition, morphology and/or physical properties. For example, if excitation waveform 24 produces an acoustic waveform that includes multiple acoustic frequency components, then excitation waveform 24 may be used to characterize multilayer assemblies with irregularly-spaced layers or features. Alternatively, or in addition, excitation waveform 24 may be used to study structures which act as acoustic waveguides, or acoustic bandgap materials.

In some embodiments, pulse shaper 14 may also be used to adjust the properties of each of the pulses comprising excitation waveform 24. For example, if pulse shaper 14 includes a liquid crystal SLM and appropriate polarization optics, the pulse shaper may be used to individually adjust the polarization of each of the pulses in excitation waveform 24.

Delays between pulses comprising excitation waveform 24 may be adjusted to investigate the frequency-dependence of one or more properties of sample 16. The response of the sample to acoustic excitation may be enhanced by suitably setting the delays between pulses, and the sample response may be maximized by iteratively adjusting said delays. For example, a genetic or other search algorithm may be used to iteratively adjust the configuration of pulse shaper 14 to produce an excitation waveform 24 which maximizes a sample response measured by detector 18.

Probe waveform 22 is generated by laser source 12 and may be phase-coherent and temporally synchronized and/or delayed with respect to input waveform 20. In general, probe waveform 22 may include one or more optical pulses, and the one or more optical pulses may comprise a sequence of pulses similar to the sequence of pulses comprising excitation waveform 24. Probe waveform 22 may be generated from excitation waveform 24 by means of a beamsplitter or other similar device. If probe waveform 22 includes a sequence of pulses that are similar with respect to their temporal spacings as the pulses of excitation waveform 24, then an enhancement of the signal measured by probe waveform 22 may be obtained since each successive cycle of the propagating acoustic wave in sample 16 would produce signal that would be imparted to each successive pulse in the probing sequence. The overall delay of the pulse sequence comprising probe waveform 22 may be optimized, and then acoustic measurements could be conducted as frequency-domain measurements, with little or no further adjustment in the overall delay of the probe pulse sequence relative to the excitation pulse sequence, and systematic variation in the pulse sequence repetition rate (i.e. the acoustic frequency). Minor adjustments in the timing of probe waveform 22 could be made for phase cycling or in order to maintain the largest possible measurement signal intensity with respect to the phase relationship between the acoustic waveform propagating within sample 16 and probe waveform 22.

A radiation frequency which corresponds to an optical frequency of probe waveform 22 may be absorbed by sample 16. In general, the optical frequencies of input waveform 20 and probe waveform 22 may be the same, or the optical frequency of one waveform may differ from that of the other. For example, the optical frequency of probe waveform 22 may correspond to the second harmonic frequency of the optical frequency of input waveform 20. In this aspect, laser source 12 may additionally include optical elements such as nonlinear crystals, lenses, beamsplitters, and other elements suitable for generating multiple phase-coherent output waveforms at different optical frequencies.

Probe waveform 22 may be incident upon either the front or rear surface of sample 16, wherein the front surface is defined as the surface upon which excitation waveform 24 is first incident. Interaction of probe waveform 22 with sample 16 generates measurement waveform 26, wherein one or more properties of measurement waveform 26 may be different from those of probe waveform 22. For example, the optical phase of measurement waveform 26 may be modulated relative to the optical phase of probe waveform 22. Alternatively, the temporal intensity profile of measurement waveform 26 may be different from the temporal intensity profile of probe waveform 22.

Detector 18 measures the changes in measurement waveform 26 relative to probe waveform 22 and converts said changes into a signal, such as an electronic signal, which may be further processed. For example, detector 18 may include an interferometer for detecting the phase shift introduced in measurement waveform 26 (relative to probe waveform 22) by the acoustic waveform in sample 16 produced by excitation waveform 24. The phase shift may be detected at the front or rear surface of sample 16. Alternatively, for example, detector 18 may include optical and electronic elements suitable for measuring time-resolved reflectivity, transmission, beam deflection, lensing, diffraction, refraction, and/or changes in spectral content of measurement waveform 26, relative to probe waveform 22. Measurements which may be used to characterize one or more properties of sample 16 include, but are not limited to, time-resolved scattering, absorption, emission, second-harmonic generation, and other signals which arise from the response of sample 16 to excitation waveform 24, and are extracted from measurement waveform 26. The means for detecting measurement waveform 26 and converting the waveform into electronic signal 30 may be embodied in detector 18.

Electronic processor 28 receives signal 30 from detector 18 and uses signal 30, which contains information about the acoustic response of the sample at one or more measurement acoustic frequencies, to determine information about the sample. Electronic processor 28 may include control elements for electronically controlling and adjusting the configuration of detector 18 and/or pulse shaper 14. Electronic processor 28 may also include hardware and software means for determining, based on signal 30, one or more electronic control signals to send to detector 18 and/or pulse shaper 14.

Ultrafast laser pulses may be temporally and spatially shaped using techniques such as frequency domain pulse shaping methods, which employ modulation devices such as liquid crystal spatial light modulators. Output optical waveforms generated in this manner may, for example, include multiple pulses which form a sequence extending over a time window of a few tens of picoseconds, and may produce an ultrahigh frequency acoustic waveform upon interaction with the sample.

Figure 2A:
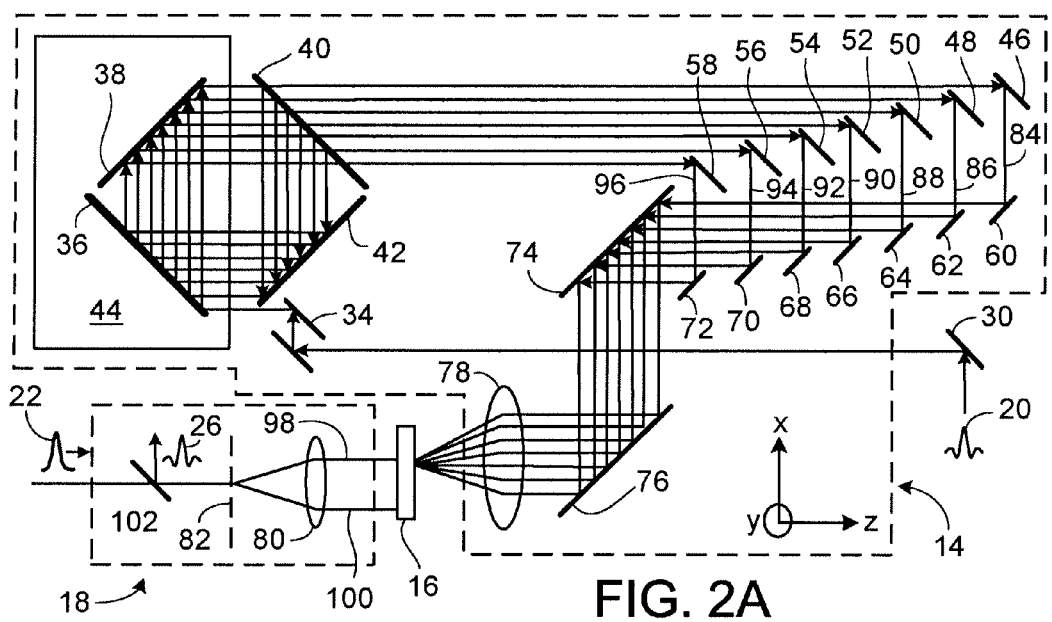
FIG. 2A is a schematic diagram of a 7-beam recirculating pulse shaper and interferometric detection apparatus for the generation of narrowband acoustic waves, and the measurement of one or more properties of a sample using the waves.

One embodiment of a recirculating pulse shaper, shown in FIG. 2A, provides an alternate system for producing optical waveforms suitable for the generation of ultrahigh frequency acoustic waveforms of tunable frequency. The system includes: (i) a pulse shaper 14, consisting of a 7-beam adjustable recirculating cavity and retroreflectors; (ii) output mirrors and at least one focusing lens; and (iii) an interferometric detection apparatus 18 for the measurement of the acoustic frequency-dependence of one or more sample properties. Pulse shaper 14 generates optical pulse sequences at a range of repetition frequencies, where the frequency may be adjusted by changing the length of the recirculating cavity. For example, in the present embodiment, pulse sequences with frequencies in the range 2-2000 GHz are employed to generate acoustic waves in a sample. The acoustic wave generated in sample 16 has an acoustic frequency that may be similar to the repetition frequency of the waveform.

Referring to FIG. 2A, input waveform 20, generated by a laser source (not shown), is guided by mirrors 30, 32 and 34 into the adjustable recirculating cavity of pulse shaper 14. Mirrors 36, 38 and 42, together with output interface 40, comprise the cavity. Mirrors 36 and 38 are mounted on adjustable delay stage 44. Input waveform 20, which may include one or more pulses, reflects from the surfaces of mirrors 36 and 38 and is incident upon output interface 40. A portion of the light intensity of input waveform 20 is transmitted through output interface 40 and a portion is reflected from the surface of output interface 40. The portion that is transmitted, beam 84, is directed by mirrors 46, 60, 74 and 76 into lens 78, which focuses beam 84 onto the surface of sample 16. The reflected portion continues in a path around the cavity, reflected further by mirrors 42, 36 and 38 and once again impinging upon output interface 40 at a spatial location which is displaced in the x direction (i.e., horizontally) from the previous incident location.

As before, a portion of the light intensity incident upon output interface 40 is transmitted as beam 86, and is directed and focused by mirrors 48, 62, 74 and 76, and lens 78, to the same spot on the surface of sample 16 to which beam 84 was previously focused. The remaining portion of the light intensity reflects from the surface of output window 40 and circulates around the cavity again.

In this manner, seven individual beams 84, 86, 88, 90, 92, 94 and 96 emerge from the recirculating cavity and are directed by mirrors 46, 48, 50, 52, 54, 56, 58, 60, 62, 64, 66, 68, 70, 72, 74 and 76, and focused by lens 78, onto the same spot on the surface of sample 16. Together, the seven beams comprise excitation waveform 24.

A single adjustment of delay stage 44 increases or decreases the delay between successive pulses in excitation waveform 24, thereby changing the repetition frequency of the sequence of pulses. Due to the symmetry of the cavity, the spacings between successive pulses comprising excitation waveform 24 are the same, or nearly the same.

Figure 2B:
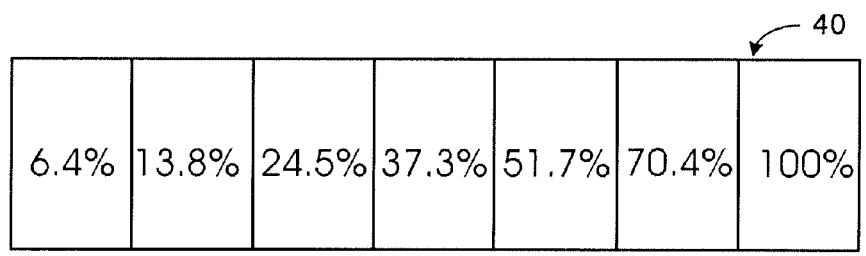
FIG. 2B is a schematic diagram of an output window with spatially varying transmission that is employed in a recirculating cavity pulse shaper.

Output interface 40 is constructed such that a sequence of 7 pulses emerges from pulse shaper 14 with a temporal intensity envelope that is substantially Gaussian in shape, assuming that input waveform 20 is a single pulse having a temporal duration that is substantially shorter than the beam recirculation time within the cavity of pulse shaper 14. For example, output interface 40 may be an output window, where the reflectivity of the output window varies along at least one spatial dimension of the window. FIG. 2B is a schematic of one example of output window 40, showing the relative percent transmission at each spatial location on the surface of the window. The reflectivity of the window varies along the spatial x-dimension. For example, at the location on the window where the recirculating beam is first incident, 6.4% of the incident light intensity is transmitted, and the balance is reflected. At the spatial location upon which the recirculating beam is incident on its second pass, 13.8% of the light intensity is transmitted, and the balance is reflected. There are seven distinct regions of differing transmission on the surface of the output window, each corresponding to one of the output pulses from pulse shaper 14. The temporal intensity envelope of the pulse sequence comprising excitation waveform 24 depends on the temporal duration of input waveform 20 entering pulse shaper 14 and the spatially-dependent transmission pattern of output interface 40. If the temporal duration of input waveform 20 is substantially shorter than the beam recirculation time in the cavity of pulse shaper 14, then the temporal intensity envelope of the pulse sequence comprising excitation waveform 24 depends mostly upon the spatial transmission pattern of output window 40.

Figure 2C:
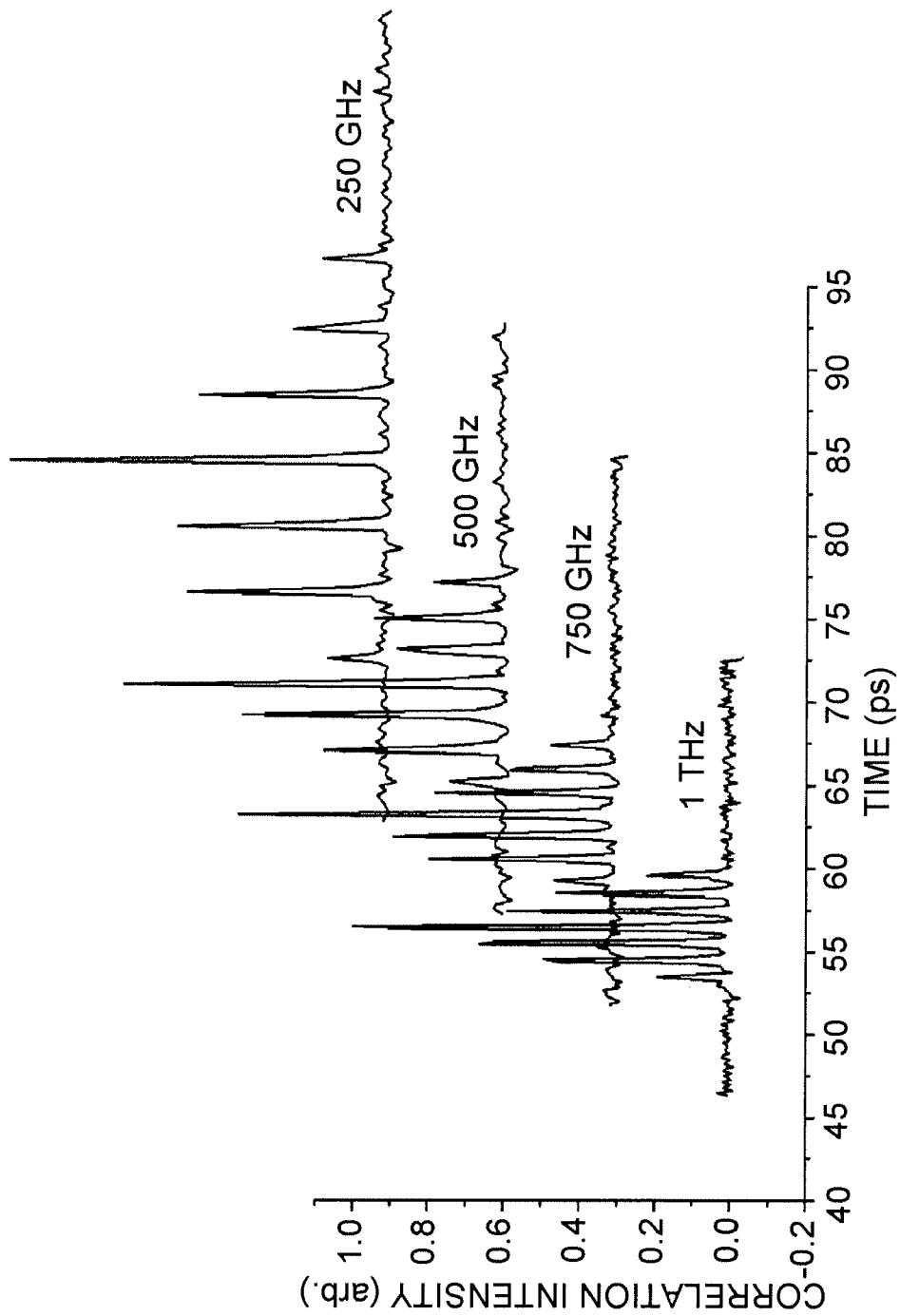
FIG. 2C is a graph showing a measurement of the cross-correlation intensity between a reference pulse and four different pulse trains generated in a recirculating cavity pulse shaper.

FIG. 2C shows the results of cross-correlation measurements between a reference pulse and four different optical pulse trains, each corresponding to an excitation waveform 24 and each produced by adjusting the cavity of the recirculating retroreflecting pulse shaper 14 to a different length by changing the position of delay line 44. The temporal intensity envelope of each waveform is approximately Gaussian in shape.

In the embodiment shown in FIG. 2A, detector 18 is an interferometric detector, and is employed to monitor the phase shift of measurement waveform 26, relative to probe waveform 22, in response to surface displacements induced by the acoustic wave generated in the sample 16 by excitation waveform 24. Probe waveform 22 is incident upon phase mask 82 and is diffracted into +1 and −1 diffraction orders by the mask. The diffracted orders are collimated and made to propagate along parallel paths by lens 80 and the configuration of detector 18 is adjusted such that one of these orders, such as the +1 order 98, is incident upon the rear surface of sample 16 at a location that is opposite or nearly opposite the position on the front surface of the sample upon which the 7 beams of excitation waveform 24 are incident. The other beam 100 diffracted from mask 82 is incident upon the rear surface of sample 16 at a spatial location which is well separated from the location at which beam 98 is incident.

The 7 beams of excitation waveform 24 generate an acoustic wave in sample 16 that propagates from the front to the rear surface, displacing the rear surface from its equilibrium (unperturbed) position and thereby contributing a phase shift to beam 98, the magnitude of which is dependent upon the amplitude of the generated acoustic wave, the time delay between input waveform 20 and probe waveform 22, and other properties of sample 16.

Beams 98 and 100 reflect from the surface of sample 16 and are recombined by lens 80 and phase mask 82 such that the two waveforms are spatially and temporally coincident after passage through phase mask 82. The superposition of beams 98 and 100 generates measurement waveform 26, wherein the temporal and spatial shape of measurement waveform 26 arises from optical interference between beams 98 and 100. The modulation of measurement waveform 26 includes a signal component that characterizes one or more properties of sample 16, wherein the one or more properties are characterized at an acoustic frequency defined by the inverse of the temporal spacing of the pulses in excitation waveform 24.

Measurement waveform 26 is diverted by beamsplitter 102 for further processing. For example, measurement waveform 26 may be imaged using a CCD camera. Alternatively, for example, measurement waveform 26 may be converted to an electronic signal using a photodiode or other similar device within detector 18. The electronic signal may be further processed by electronic processor 28.

In general, delay stage 44 and any of mirrors 36 and 38 mounted thereon may be replaced by any optical element or sequence of elements which introduce(s) an additional propagation delay to input waveform 20 as it travels around the recirculating cavity of pulse shaper 14. The length of the recirculating cavity of pulse shaper 14 may be adjusted by an electronic controller that may be a separate controller or may be embodied in processor 28. Adjustment of the cavity length may be achieved by translating delay stage 44. The adjustment may produce a pulse sequence which produces in sample 16 an acoustic waveform of a chosen frequency, and the adjustment may be iterative, such that the acoustic frequency is scanned in order to produce a largest or smallest measured sample response due to the acoustic waveform.

The recirculating pulse shaper shown in FIG. 2A includes 7 beams. In general, pulse shaper 14 may include any number of beams, and the external optical elements of the pulse shaper, such as mirrors and lenses, may be appropriately increased or decreased in size and number to accommodate a larger or smaller number of beams.

The recirculating cavity path may be of any length. The range of frequencies to which excitation waveform 24 may correspond is limited only by the total displacement range of delay stage 44 and the temporal duration of input waveform 20. In the present embodiment, the cavity path length may be resized to provide temporal separations of between 500 fs and 500 ps, limiting the acoustic frequency range to 2-2000 GHz. In general, however, the acoustic frequency to which excitation waveform 24 corresponds may be any acoustic frequency, such as 500 GHz, 1 THz, 3 THz or more; or 100 GHz, 10 GHz, 1 GHz, 100 MHz, or less. The recirculating cavity length may be adjusted to any length to produce a sequence of pulses corresponding to excitation waveform 24, which generates an acoustic wave of a desired frequency.

Input waveform 20 may include an output waveform derived from laser source 12 that is temporally compressed to its transform limit, or alternatively, may include a waveform from laser source 12 that is only partially temporally compressed, or even stretched, prior to entering pulse shaper 14. For example, input waveform 20 may include a waveform from laser source 12 that has been stretched in a dual-grating pulse stretcher prior to entering pulse shaper 14, such that the emerging shaped excitation waveform 24 represents only about a 50% duty cycle relative to input waveform 20. The system shown in FIG. 2A may additionally comprise said optical pulse stretcher/compressor prior to mirror 30 along the path of input waveform 20. The pulse stretcher/compressor may be used to lengthen or shorten the duration of input waveform 20 before the waveform enters pulse shaper 14. Lengthening or shortening of the duration of input waveform 20 may include imparting amplitude-only modulation, or phase-only modulation, or both phase and amplitude modulation to the spatially-dispersed frequency components of input waveform 20. The pulse stretcher/compressor may include, for instance, two parallel holographic gratings separated by a distance that is adjustable by means of a delay line, and may also include one or more devices for modulating the frequency components of input waveform 20, such as an SLM, MEMS device, deformable mirror, or fixed patterned mask. The stretcher/compressor may be used to tune the duty cycle of the optical pulse train comprising excitation waveform 24, in order to broaden or narrow the frequency content of the waveform.

Output interface 40 may be an optical window fabricated such that a portion of the optical beam intensity incident at any point on the beamsplitter front surface may be transmitted, and the remaining portion reflected from the beamsplitter. The ratio of transmitted (T) to reflected (R) light intensity may be any ratio, and may be different at different spatial positions on the surface of the window. The spatially dependent T/R ratio may be designed and fabricated in order to produce an excitation waveform 24 with any particular temporal intensity envelope. In general, the temporal intensity envelope of the pulse train comprising excitation waveform 24 may be complicated.

Alternatively, output interface 40 may include any other element or combination of elements which permit a portion of the recirculating beam within pulse shaper 14 to emerge each time the beam is incident upon interface 40. The element or combination of elements may be adjustable, and may be configured to produce a specific spatially-dependent transmission profile.

Mirrors 74 and 76, and lens 78, may be replaced by a reflective, curved mirror, such as a spherical or parabolic mirror. Phase mask 82 may be replaced by any other element which diffracts input waveform 22 into multiple diffraction orders. For example, phase mask 82 may be replaced by a diffraction grating. Alternatively, phase mask 82 and lens 80 may be replaced by one or more optical elements that convert input waveform 22 into two beams 98 and 100 and upon reflection of the two beams from the surface of sample 16, recombine beams 98 and 100 to produce measurement waveform 26 which is modulated due to optical interference between beams 98 and 100. For example, said optical elements may include one or more beamsplitters, mirrors and lenses.

Where beams 98 and/or 100 are generated by diffraction, diffracted beams corresponding to any diffraction order(s) may be used. For example, the ±2 diffraction orders may be used. Different diffraction orders may be used for beams 98 and 100, such as, for example, the +2 and −1 orders. The design of the phase mask or other diffractive element which generates beams 98 and 100 may be optimized to produce maximum intensity beams in particular diffracted orders. For example, phase mask 82 may be optimized to produce the highest intensity in the +1 and −1 diffracted orders.

The interferometer embodied in detector 18 may be configured such that beams 98 and 100 are incident on the front surface of sample 16. Such a configuration may be useful, for example, when measuring samples with thick or poor optical quality rear surfaces. In other embodiments, a different arrangement for interferometric detection may be employed. For example, sample 16 may be incorporated into one arm of a Mach-Zehnder interferometer or a Michaelson interferometer.

Figure 3A:
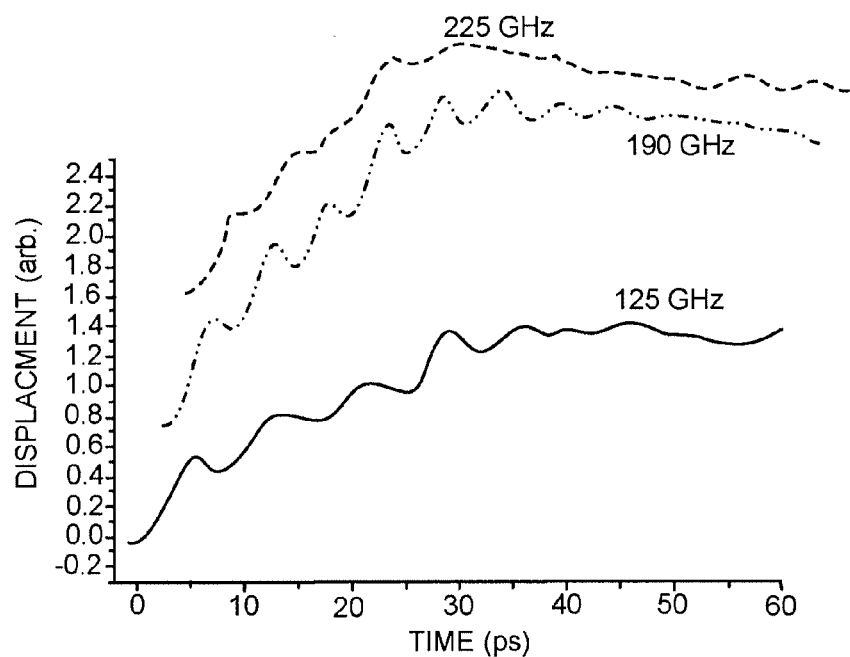
FIG. 3A is a graph showing the displacement from its equilibrium position of the surface of a thin aluminum film as a function of time, in response to acoustic waveforms at three different acoustic frequencies propagating through the film.

Narrowband acoustic waves generated by absorption of optical waveforms such as those produced by pulse shaper 14 may be used to characterize one or more properties of a sample 16. For example, narrowband acoustic measurements may be used to determine the thickness of a uniform sample to high accuracy, and with high resolution. FIG. 3A shows the results of an interferometric measurement of the surface displacement of a sample comprising an aluminum film on a sapphire substrate. Narrowband acoustic waves at three different frequencies—225 GHz, 190 GHz and 125 GHz—were generated in the aluminum film. The output waveforms which were used to generate acoustic waves at these frequencies were produced by appropriate adjustment of the recirculating cavity in pulse shaper 14. The oscillating component of the interferometric signal was largest at an acoustic frequency of 190 GHz. At this frequency, the oscillating signal was large in amplitude during the first 7 cycles, which corresponded to the arrival of the 7 pulses comprising excitation waveform 24. The oscillating signal also continued after the last pulse had been absorbed, indicating that the aluminum film was undergoing acoustic "ringing" (indicated by the arrow in FIG. 3A) since the period of excitation waveform 24 matched the round-trip time of the acoustic pulses inside the film. The 190 GHz acoustic wave matched a resonance condition for the aluminum film which corresponded to the film thickness. The acoustic waves at 225 GHz and 125 GHz did not match the aluminum film resonance, and there was no ringing at these frequencies.

Acoustic resonance may be used to determine the film thickness. The frequency of the narrowband acoustic wave may be changed by appropriate adjustment of pulse shaper 14, and the surface displacement of the sample recorded interferometrically. The acoustic frequency which produces the largest amplitude ringing corresponds most closely with the thickness of the sample, since acoustic resonance within the sample causes large sample surface displacements even after excitation waveform 24 has been absorbed. In samples which include multiple layers, more than one acoustic resonance frequency may be determined by adjusting the repetition rate of the pulse sequence of excitation waveform 24, and the multiple acoustic resonance frequencies may correspond to the thicknesses of multiple sample layers.

Figure 3B:
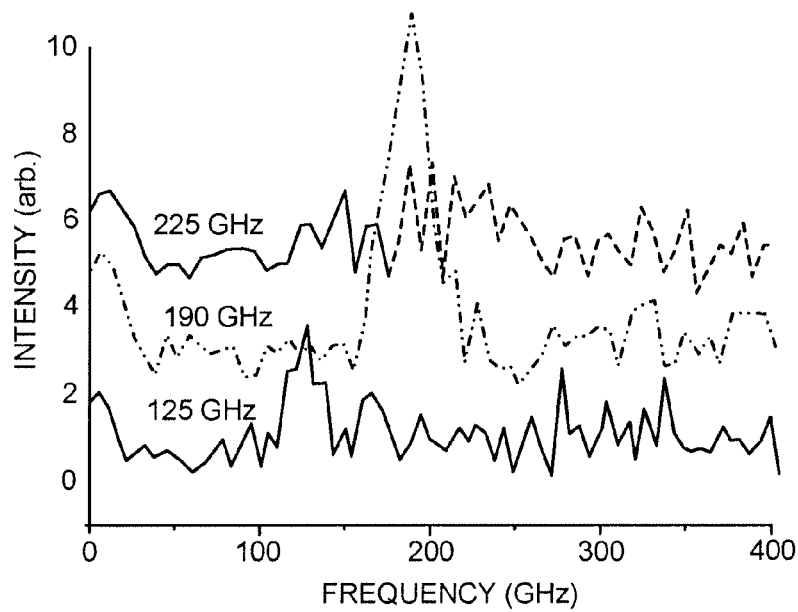
FIG. 3B is a graph showing a Fourier transform of the time-dependent surface displacement data shown in FIG. 3A.

Determination of the acoustic frequency which produces the largest surface displacement may be accomplished by Fourier transforming the portion of the time-dependent displacement signal for which excitation of the sample has already been completed. FIG. 3B shows the Fourier spectrum of the portion of the time-dependent displacement signal of FIG. 3A following the arrival of the last of the 7 excitation pulses. The Fourier transform signals clearly show a maximum sample response near 190 GHz. The surface displacement of the sample is a maximum at an acoustic driving frequency of about 190 GHz, indicating that 190 GHz corresponds to a resonance condition for the aluminum film. From the resonance frequency $f_{res}$, the thickness of the sample is calculated according to $$f_{res} = \frac{v_s}{2d} \tag{1}$$

where $v_s$ is the velocity of sound in the sample, and d is the sample thickness. Based on the measurements shown in FIG. 3A, and using equation (1), the film thickness d was calculated to be 17.1±0.3 nm, in excellent agreement with an independent measurement of the film thickness by high-resolution profilometry, which yielded 17.6 nm. The overall measurement error is only about 3%, at very high resolution.

Figure 4A:
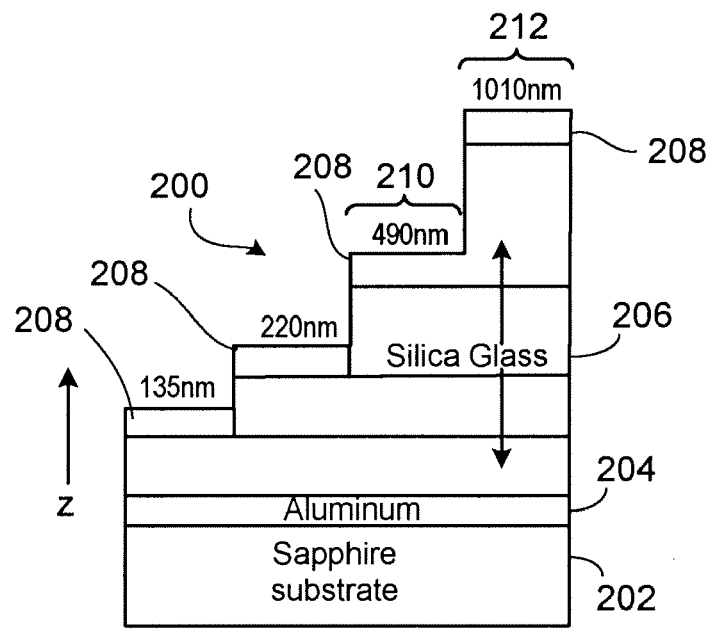
FIG. 4A is a schematic diagram showing the structure of a "sandwich" sample used to determine the acoustic frequency-dependent attenuation and sound velocity in silica glass.

Narrowband acoustic measurements may also be used to determine properties of samples such as frequency-dependent acoustic velocities and damping rates. For example, a sample 200 constructed to determine the acoustic velocity and damping rate in silica glass is shown in FIG. 4A. The sample is a "sandwich" structure that includes an "excitation" aluminum film 204 deposited on top of a sapphire substrate 202. Silica glass 206 in various thicknesses is deposited on the aluminum film to form a step-like surface, and then each of the "steps" is coated with a "detection" aluminum film 208, where the thickness of aluminum deposited on the surface of each of the steps is the same. The different steps correspond to different thicknesses of silica glass, but have the same aluminum transducer thicknesses. For example, step 210 corresponds to a silica glass thickness of 490 nm, and step 212 corresponds to a silica glass thickness of 1010 nm.

Figure 4B:
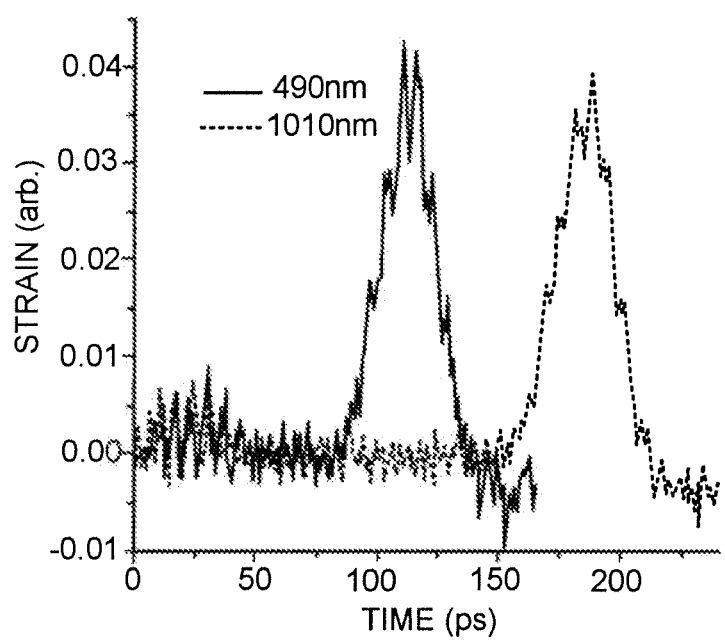
FIG. 4B is a graph showing the acoustic strain in two different thicknesses of silica glass in the sample of FIG. 4A, as a function of time.

By generating narrowband acoustic waves at a given frequency in a material sample and allowing the waves to travel through different thicknesses of material, as in the step-like structure of sample 200, the acoustic velocity and damping constant may be determined. FIG. 4B shows an interferometric measurement of strain in sample 200 at an acoustic frequency of 150 GHz. Excitation waveform 24, comprising a 7-pulse sequence with pulses temporally spaced to produce a 150 GHz acoustic wave, was focused onto the surface of the excitation film 204. A longitudinal acoustic wave was generated, and subsequently propagated through the silica glass. Interferometric detection was employed, with beams 98 and 100 focused on the surface of the detection film 208 in order to monitor time-dependent displacements of the surface from its equilibrium position. The strain η was calculated according to $$\eta(z,t) = \frac{\partial u}{\partial z} = \frac{1}{v_s}\frac{\partial u}{\partial t} \tag{2}$$

where the displacement u of the detection film in response to the acoustic wave occurs in the z-direction.

The measurements in FIG. 4B were recorded from steps 210 and 212, and corresponded to silica glass thicknesses of 490 nm and 1010 nm respectively. Both the temporal position and the intensity of the strain response at step 212 are different from the values at 210. Taking the Fourier transforms of the time-resolved strain responses in FIG. 4B and comparing their spectral intensity I at the driving frequency $\omega_0$=150 GHz, the acoustic damping rate α may be determined from $$\alpha(\omega_0) = \frac{1}{\Delta d_{SiO_2}} \ln \left| \frac{I_{490nm}(\omega_0)}{I_{1010nm}(\omega_0)} \right| \tag{3}$$

where $I_{490\ nm}$ and $I_{1010\ nm}$ are the spectral intensities corresponding to the signals from steps 210 and 212 respectively, and $\Delta d_{SiO2}$ is the difference in thickness of the silica glass between these two steps. Acoustic damping at frequency $\omega_0$ may indicate the presence of dynamical spectral features in silica glass at $\omega_0$, or of structural features at a wavevector $q=2\pi/\omega_0$.

The difference in times-of-flight τ of the acoustic strain responses in FIG. 4B may be used to determine the acoustic velocity $v_{SiO2}$ according to $$v_{SiO_2}(\omega_0) = \frac{\Delta d_{SiO_2}}{\tau_{1010nm}(\omega_0) - \tau_{490nm}(\omega_0)} \tag{4}$$

The acoustic velocity may then be further used to calculate, for instance, elastic properties such as the acoustic impedance and bulk modulus of silica glass at frequency $\omega_0$.

Figure 5A:
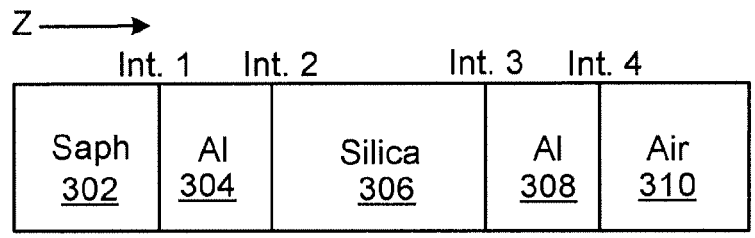
FIG. 5A is a schematic diagram of a sample comprising multiple layers, wherein the thicknesses of one or more layers of the sample are unknown.

High frequency, narrowband acoustic waves may also be used to investigate material samples comprising multiple layers, and/or samples with unknown sub-surface structural features. An example of a multilayer sample 300 is shown in FIG. 5A. A sapphire substrate 302 was coated with layers of aluminum 304, silica glass 306, and then aluminum 308 again, yielding a sandwich-type structure of three layers surmounted on sapphire on one side, and exposed to the air 310 on the other. The interfaces between specific layers are also labeled in the figure. For example, interface 1 is located between sapphire substrate 302 and aluminum layer 304.

The thickness, sound velocity, or other properties of each of these layers may be determined using narrowband, high frequency acoustic measurements and numerical techniques to extract the relevant quantities.

Excitation waveform 24 was focused to the surface of aluminum layer 304 and generated, through optical absorption, an acoustic wave which propagated along the z-axis. Interferometric detection was employed by focusing beams 98 and 100 onto the surface of aluminum film 308, i.e. detection occurred on the rear surface of sample 300. The amplitude of the acoustic wave, detected as displacements of the surface of aluminum film 308 from its equilibrium position, depended upon the amplitude of the initial acoustic wave, the reflection and transmission coefficients at all interfaces within sample 300, the acoustic damping of each of the layers, the temporal delay associated with propagation of the acoustic wave through the various layers, and other properties of the sample. The analysis of the interferometric signal was most easily performed in the frequency domain, and subsequently Fourier-transformed in order to compare with the time-domain measurement.

A frequently used technique for numerically analyzing the elastic properties of multilayer systems such as the example shown in FIG. 5A, in which acoustic waves are generated and subsequently propagate, is acoustic mismatch theory. Quantifying the propagation of acoustic waves through multilayer structures involves careful analysis of reflection and transmission coefficients at each interface, as well as frequency-dependent acoustic velocities and damping rates, which may be complicated by the presence of sample structural features. Narrowband measurements may be used to simplify consideration of the frequency dependence, providing the bandwidth of the acoustic pulse generated in sample 300 remains sufficiently narrow.

A longitudinal acoustic wave of arbitrary profile $u_{exc}(z,t)$ was launched in sample 300 through optical absorption of excitation waveform 24 in aluminum layer 304. The frequency content of the acoustic wave immediately following generation in the aluminum film is given by the Fourier transform as $$u_{exc}(z, \omega) = \frac{1}{2\pi} \int_{-\infty}^{\infty} u_{exc}(z, t) e^{i\omega t} dt \quad (5)$$

As the acoustic wave travels through the aluminum layer and into the layer of silica glass, it undergoes partial transmission and reflection at the interface between the layers. The magnitudes of the transmission and reflection coefficients at the interface are determined by the mismatch of the acoustic impedance $Z=v\rho$ of the two materials, where $v$ is the sound velocity in a particular material and $\rho$ is the density of the material. The reflection $r^+$ and transmission $t^+$ coefficients at the aluminum-silica glass interface are given by $$r^+_{Al-SiO_2} = \frac{v_{Al}\rho_{Al} - v_{SiO_2}\rho_{SiO_2}}{v_{Al}\rho_{Al} + v_{SiO_2}\rho_{SiO_2}} \quad (6)$$

$$t^+_{Al-SiO_2} = \frac{v_{Al}\rho_{Al}}{v_{Al}\rho_{Al} + v_{SiO_2}\rho_{SiO_2}} \quad (7)$$

where the superscript "+" indicates an acoustic wave propagating in the +z-direction, i.e. from left-to-right in FIG. 5A. Coefficients corresponding to acoustic waves propagating in the opposite direction will be denoted with a superscript "−".

After partial transmission across the aluminum-silica glass interface, the acoustic wave propagates in silica glass with amplitude and phase given by $$u_{SiO_2}(z, \omega) = t^+_{Al-SiO_2} \exp\left(\frac{i\omega z}{v_{SiO_2}}\right) \quad (8)$$

where the acoustic wave travels at velocity $v_{SiO_2}$ for a distance $z=d_{SiO_2}$ corresponding to the known thickness of the silica glass layer. The acoustic wave subsequently experiences partial reflection and transmission at the interface between the silica glass layer 306 and the aluminum layer 308.

Figure 5B:
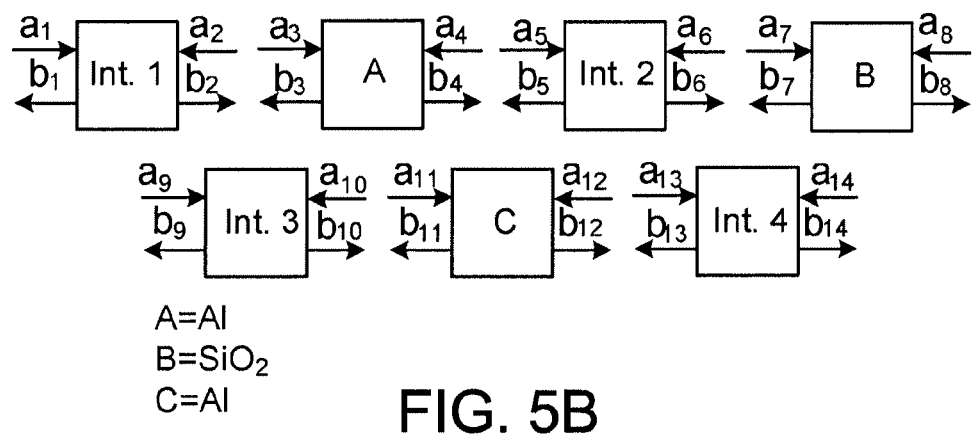
FIG. 5B is a schematic diagram of the reduction of the sample of FIG. 5A to a series of interfaces and material slabs containing acoustic inputs and outputs, in order to analyze the measured interferometric signal from the sample which arises as a result of introducing an acoustic waveform therein.

To calculate the frequency-domain interferometric signal $u_{sig}(z,\omega)$, the system is reduced to a series of components for which the input and output acoustic waveforms may be calculated. FIG. 5B is a schematic illustration of this process for sample 300 shown in FIG. 5A. The coefficients $a_i$ and $b_i$ describe the inputs and outputs, respectively, to the various layers and interfaces comprising sample 300. The sapphire and air portions of sample 300 are acoustically decoupled from the rest of the system, so these layers are not included in the analysis. From the figure, the signal $u_{sig}(z,\omega)$ is measured at the aluminum-air interface 4, as the output $b_{14}$. A system of coupled equations describing the propagation of acoustic waves throughout the multilayer sample 300 may be written as $$b_2 = b_3 r_1^- \quad (9)$$

$$b_3 = \exp(i\eta d_A v_A^{-1}) b_5$$

$$b_4 = \exp(i\eta d_A v_A^{-1}) b_2$$

$$b_5 = b_4 r_2^+ + b_1 t_2^-$$

$$a_5 = b_4 t_2^+ + b_1 t_2^- - b_6$$

$$b_7 = \exp(i\eta d_B v_B^{-1}) b_9$$

$$b_8 = \exp(i\eta d_B v_B^{-1}) b_6$$

$$b_9 = b_8 r_3^+ + b_{11} t_3^-$$

$$b_{10} = b_8 t_3^+ + b_{11} r_3^-$$

$$b_{11} = \exp(i\eta d_C v_C^{-1}) b_{13}$$

$$b_{12} = \exp(i\eta d_C v_C^{-1}) b_{10}$$

$$b_{13} = b_{12} r_4^-$$

$$b_{14} = b_{12} t_4^+$$

In equations (9) above, $d_i$ represents the thickness of layer i and $v_i$ represents the acoustic velocity in the layer.

The system of equations (9) may be solved numerically to yield one or more quantities which characterize properties of the multilayer sample 300. The numerical solution may take the form of a least-squares or other minimization routine which adjusts the values of the unknown quantities. For example, the frequency-domain acoustic output signal is determined directly from equations (9) as $$u_{sig}(z,\omega) = b_{14}(z,\omega) \quad (10)$$

The time-domain interferometric displacement signal and strain may be calculated from $$u_{sig}(z, t) = 2\pi \int_{-\infty}^{\infty} b_{14}(z, \omega)e^{-i\omega t}d\omega \quad (11)$$

$$\eta_{sig}(z, t) = \frac{\partial u_{sig}(z, t)}{\partial t}$$

Figure 5C:
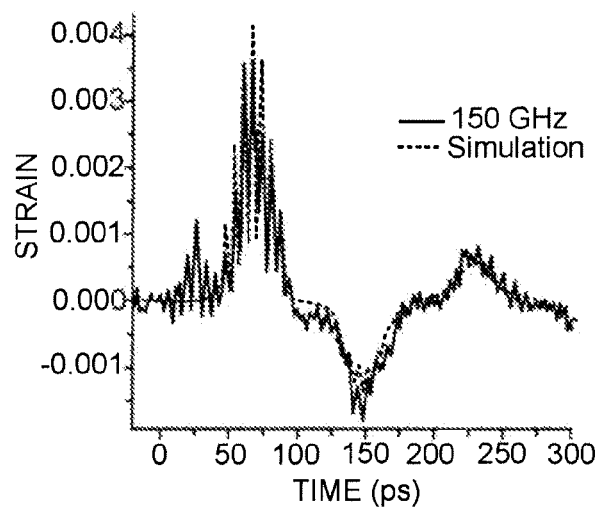
FIG. 5C is a graph showing the acoustic strain in the sample of FIG. 5A, where the strain is determined through measurements at an acoustic frequency of 150 GHz, and also calculated using a mathematical model of the sample.

The numerical minimization routine may, for example, vary the numerical values of one or more parameters in equations (9) so that the differences between the measured interferometric displacement or strain and the values calculated from equations (11) correspond to a minimum error condition. FIG. 5C shows measured and calculated strain data at an acoustic frequency of 150 GHz for sample 300. For the example shown in the figure, the thicknesses of both aluminum layers, $d_A$ and $d_C$, were known, but the thickness of the silica glass layer $d_B$ was unknown. Solving equations (9) with iterative adjustment of the value of $d_B$ within a minimum-error constraint yielded the best-fit simulation data of FIG. 5C and a silica glass thickness of 210 nm.

It is clear from the size of the data set in FIG. 5C that the system of equations (9) is strongly over-determined. Therefore, the values of more than one parameter may be simultaneously retrieved through analysis of the interferometric data by, for example, a nonlinear least-squares minimization routine. For example, all three thicknesses $d_A$, $d_B$ and $d_C$ may be simultaneously found by calculating the best-fit displacement or strain, as in FIG. 5C. Alternatively, for example, other quantities of interest, such as the sound velocities $v_A$, $v_B$ and $v_C$ may be determined through this method. As before, the concentration of most of the acoustic energy into a narrow frequency band may provide greater signal-to-noise in the measurement data, relative to broadband photoacoustic spectroscopy.

Figure 6:
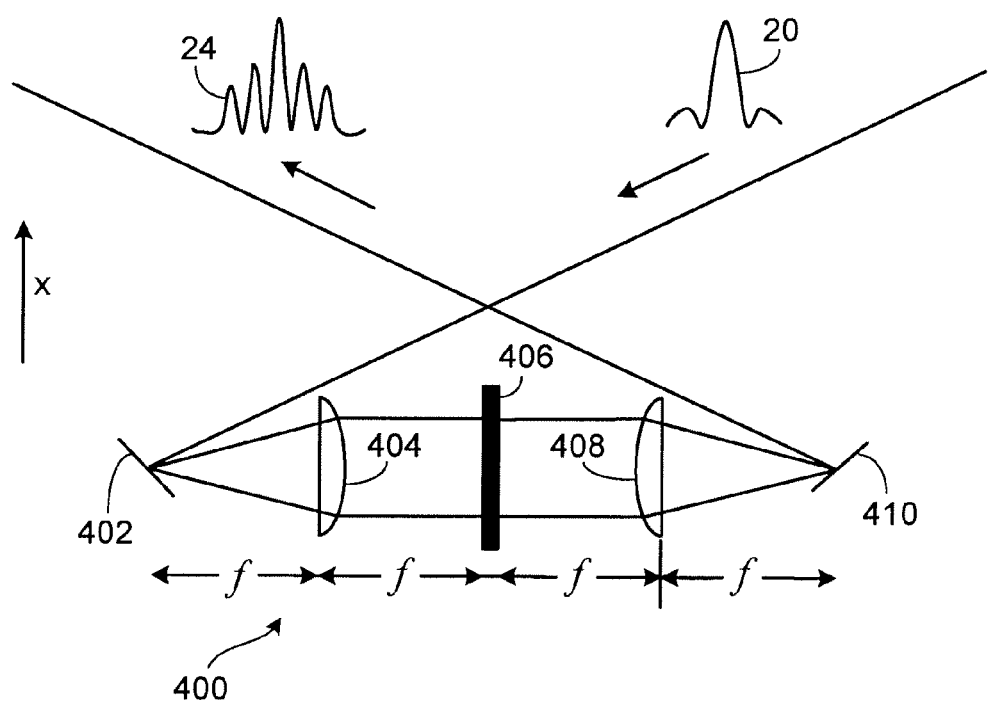
FIG. 6 is a schematic diagram of a frequency-domain pulse shaper that may be used to generate optical pulse sequences for generating acoustic waves in a sample.

In the specific embodiment shown in FIG. 2A, a 7-beam recirculating pulse shaper was used to generate a sequence of optical pulses suitable for launching an acoustic waveform in a sample. Exemplary embodiments may employ alternative methods for providing a suitable sequence of pulses. For example, FIG. 6 is a schematic diagram of an embodiment of a Fourier domain pulse shaper 400 that may be used to generate an optical pulse sequence that is used for acoustic waveform generation in a sample. Methods and apparatus for Fourier domain pulse shaping are disclosed, for example, in U.S. Pat. No. 5,682,262 entitled "METHOD AND DEVICE FOR GENERATING SPATIALLY AND TEMPORALLY SHAPED OPTICAL WAVEFORMS", and in U.S. Pat. No. 5,719,650 entitled "HIGH-FIDELITY SPATIAL LIGHT MODULATOR", the contents of both of which are incorporated herein by reference.

Referring to FIG. 6, input waveform 20 is incident upon diffraction grating 402 which is positioned and oriented such that grating 402 disperses the frequency components comprising input waveform 20 along the spatial x axis. Lens 404 collimates the dispersed frequency components and focuses each component to its minimum spatial extent along the x dimension in the plane of modulator 406. Modulator 406 may introduce phase and/or amplitude modulation of the spatially-dispersed frequency components. Following passage through modulator 406, the frequency components are recombined by lens 408 and grating 410 such that they are spatially coincident and comprise excitation waveform 24, where excitation waveform 24 is a waveform suitable for generating an acoustic waveform in a sample.

In some embodiments, lenses 404 and 408 are cylindrical lenses of focal length f, oriented such that the curved dimension of each lies principally along the x axis. Gratings 402 and 410, lenses 404 and 408, and modulator 406 are positioned relative to one another, as shown in FIG. 6, such that the distance between successive elements is about f.

In general, gratings 402 and 410 may be the same or different. Each may be a diffraction grating, a prism, a phase mask, or any other element or combination of elements that disperses the frequency components of input waveform 20 along the spatial x dimension. Lenses 404 and 408 may have the same or different focal lengths, and either or both may be replaced by curved mirrors. The spacings between gratings 402 and 410, lenses 404 and 408, and modulator 406, where these elements are positioned as shown in FIG. 6, may all be the same, or may not all be the same.

Modulator 406 may be a liquid crystal spatial light modulator, and may include additional optical elements such as polarization optics. Alternatively, modulator 406 may be a fixed patterned mask. In some embodiments, pulse shaper 400 may be configured in a reflective geometry, wherein modulator 406 may be a MEMS device, for example, or a deformable mirror. Generally, modulator 406 is an element or combination of elements that may be transmissive or reflective, and that modulates the phase and/or amplitude of input waveform 20 such that excitation waveform 24 may be used to generate a suitable acoustic response in a sample. Modulator 406 may also include an electronic controller and hardware and software therein.

Excitation waveform 24 may include, for example, a sequence of optical pulses, wherein the temporal duration of each pulse in the sequence is similar to the temporal duration of input waveform 20, and the temporal spacings between each pulse and its predecessor may all be the same or may not all be the same.

If pulse shaper 400 is configured in a reflective geometry, lens 408 and grating 410 may not be present, and excitation waveform 24 may reflect from modulator 406 and retrace a portion of the path of input waveform 20. Pulse shaper 400 may further include additional optical elements such as a beamsplitter to spatially isolate the beam paths of input waveform 20 and excitation waveform 24.

A number of embodiments of the invention have been described. Nevertheless, it will be understood that various modifications may be made without departing from the spirit and scope of the invention. Accordingly, other embodiments are within the scope of the following claims.

What is claimed is:

1. A method comprising:
   directing a sequence of at least three optical pulses to a sample to generate an acoustic response in the sample at a frequency corresponding to the pulse sequence;
   varying the timing of one or more of the pulses in the sequence relative to one or more other pulses in the sequence to vary the frequency of the acoustic response in the sample; and
   measuring the strength of the acoustic response as a function of the varied frequency to determine information about the sample.

2. The method of claim 1, wherein the pulse sequence comprises at least four optical pulses.

3. The method of claim 1, wherein the pulses in the pulse sequence are equally spaced in time from one another.

4. The method of claim 3, wherein the frequency corresponding to the pulse sequence is the inverse of the equally spaced timing between the pulses.

5. The method of claim 1, wherein the pulses in the pulse sequence are not all equally spaced in time from one another.

6. The method of claim 5, wherein the frequency corresponding to the pulse sequence is a frequency of a peak in a frequency transform of the time-varying intensity of the pulse sequence.

7. The method of claim 1, wherein the optical pulses comprises electromagnetic radiation in at least one of the ultraviolet, visible, and infrared spectral regions.

8. The method of claim 1, wherein the frequencies of the acoustic response are in the range of about 2 to 2000 GHz.

9. The method of claim 8, wherein the frequencies of the acoustic response are in the range of about 5 to 500 GHz.

10. The method of claim 1, wherein each of the optical pulses has a pulse width less than about 1 psec.

11. The method of claim 1, wherein varying the timing of one or more of the pulses in the sequence comprises varying the timing between each pair of consecutive pulses in the pulse sequence.

12. The method of claim 11, wherein the pulses in the pulse sequence define a repetition rate, and wherein varying the timing between each pair of pulses in the pulse sequence comprises varying the repetition rate.

13. The method of claim 1, further comprising generating the pulse sequence by directing a beam comprising at least one optical pulse to make three or more passes to a partially reflective interface configured to transmit a first portion of the pulse and reflect a second portion of the pulse.

14. The method of claim 13, wherein the partially reflective interface is part of a recirculating cavity.

15. The method of claim 14, wherein varying the timing of one or more of the pulses in the sequence comprises moving one or more of the optics in the recirculating cavity relative to one or more other optics in the recirculating cavity.

16. The method of claim 13, wherein the beam makes four or more passes to the partially reflective interface.

17. The method of claim 1, further comprising generating the pulse sequence by filtering spatially dispersed spectral components of an input waveform and recombining the filtered spectral components to form an output waveform comprising the pulse sequence.

18. The method of claim 1, wherein the pulses in the sequence contact the sample at different angles.

19. The method of claim 1, wherein measuring the strength of the acoustic response comprises directing an optical probe beam to the sample to interact with the acoustic response.

20. The method of claim 19, wherein measuring the strength of the acoustic response further comprises monitoring a change in a property of the probe beam caused by its interaction with the acoustic response in the sample.

21. The method of claim 20, wherein the change in the property of the probe beam is monitored interferometrically.

22. The method of claim 20, wherein the monitored property of the probe beam is phase, intensity, direction, or spectral content.

23. The method of claim 19, wherein the optical probe beam comprises one or more optical pulses.

24. The method of claim 23, wherein the optical probe beam comprises a sequence of pulses defining a frequency substantially equal to that of the pulse sequence used to generate the acoustic response in the sample.

25. The method of claim 1, wherein the information about the sample comprises one or more resonance frequencies of the sample.

26. The method of claim 1, wherein the sample comprises a film, and wherein the information about the sample comprises a film thickness.

27. The method of claim 1, wherein the information about the sample comprises information about at least one of: a thickness of a layer in the sample, a sound velocity in the sample, an acoustic impedance mismatch between layers in the sample, and delamination of layers in the sample.

28. A system comprising:
an optical excitation source configured to direct a sequence of at least three optical pulses to a sample to generate an acoustic response in the sample at a frequency corresponding to the pulse sequence, the optical excitation source further configured to vary the timing of one or more of the pulses in the sequence to vary the frequency of the acoustic response in the sample;
an optical detection system configured to measure the strength of the acoustic response as a function of the varied frequency; and
an electronic processor coupled to the optical detection system and configured to determine information about the sample based on the measured strength of the acoustic response as a function of the varied frequency.

* * * * *